United States Patent [19]

Schlesinger et al.

[11] Patent Number: 4,769,235
[45] Date of Patent: Sep. 6, 1988

[54] IMMUNODOMINANT EPITOPE OF THE CIRCUMSPOROZOITE SURFACE PROTEIN

[75] Inventors: David H. Schlesinger, Plainsboro, N.J.; Victor N. Nussenzweig, New York, N.Y.

[73] Assignee: New York University, New York, N.Y.

[21] Appl. No.: 695,257

[22] Filed: Jan. 28, 1985

Related U.S. Application Data

[63] Continuation-in-part of Ser. No. 574,553, Jan. 27, 1984, abandoned.

[30] Foreign Application Priority Data

Jan. 27, 1984 [GB] United Kingdom ............... 8402186
Jan. 27, 1984 [GB] United Kingdom ............... 8402211

[51] Int. Cl.⁴ ................ A61K 39/015; C07K 7/06; C07K 7/00
[52] U.S. Cl. ................................ 424/88; 530/328; 530/327; 530/329
[58] Field of Search ............... 530/351, 327, 328, 329; 424/88

[56] References Cited

PUBLICATIONS

Chemical Abstracts, vol. 101, Abstract No. 208756n, 1984.
Chemical Abstracts, vol. 103, Abstract No. 69446n, 1985.
Chemical Abstracts, vol. 101, Abstract No. 223889b, 1984.
Godson et al., Nature, vol. 305, pp. 29–33, 1983.
Dame et al., Science 228:593, 1984.
Schlesinger et al., Biochemistry 23:5665, 1984.
Coppel et al., Nature 306:751, 1983.
Koenen et al., Nature 311:382, Sep. 27, 1984.

Primary Examiner—Blondel Hazel
Attorney, Agent, or Firm—Darby & Darby

[57] ABSTRACT

Disclosed are peptides the sequence of which defines an immunodominant epitope from the repetitive immunodominant epitope region of the circumsporozoite (CS) protein of a member of the genus Plasmodium, the sequence of the peptide being shorter in length than the repeating unit of the CS protein.

10 Claims, 4 Drawing Sheets

IMMUNODOMINANT EPITOPE OF THE CIRCUMSPOROZOITE SURFACE PROTEIN

This application is a continuation-in-part of copending commonly assigned U.S. patent application Ser. No. 574,553 filed on Jan. 27, 1984 now abandoned.

INTRODUCTION TO THE DISCLOSURE

This invention relates to an immunodominant epitope within the tandem repetitive polypeptide contained in the circumsporozoite protein (i.e., the surface protein of the sporozoite stage of plasmodium parasites). This invention also relates to a peptide having an amino acid sequence analogous to that of said epitope and displaying immunochemical reactivity with monoclonal antibodies to the CS protein ("monoclonal anti-CS") substantially equivalent to that of said repetitive polypeptide. The disclosures of (a) U.S. patent Application Ser. No. 234,096, of Nussenzweig, et al, entitled MALARIA VACCINE filed on Feb. 12, 1981, and (b) U.S. patent Application Ser. No. 574,553 entitled PROTECTIVE PEPTIDE ANTIGEN of Colman et al, filed on Jan. 27, 1984 (hereinafter referred to as the Malaria Vaccine patent application and the Peptide Antigen application, respectively) are hereby incorporated by reference as if fully set forth herein.

Sporozoites are the infective stage of Plasmodium protozoan parasites. The membrane of sporozoites is covered with a protein (CS or circumsporozoite protein) which is synthesized in relatively large amounts when the parasite matures inside salivary glands of the invertebrate host, Anopheles mosquitoes. Fab fragments of monoclonal antibodies to CS proteins neutralize the infectvity of the sporozoites and prevent their attachment to target cells in vitro (Hollingdale, M. R., et al., (1982) J. Immun. 128: 1929-1930). For these reasons, the CS protein is believed to play a role in the process of invasion of the host liver cells where the sporozoites continue their life cycle and transform into the next developmental stage.

The gene that codes for CS protein of the monkey malaria parasite *P. knowlesi* has been isolated as disclosed in Ellis J., "Cloning and Expression in *E. Coli* of the Malarial Sporozoite Surface Antigen Gene From *Plasmodium knowlesi*" (1983) Nature 302: 536-538 and in the Peptide Antigen Application and its structure determined as disclosed by Ozaki, L. S., et al., (1983) *Cell* 34:815, and in the Peptide Antigen application. This protein has a unique twelve amino acid peptide segment (Gln-Ala-Gln-Gly-Asp-Gly-Ala-Asn-Ala-Gly-Gln-Pro) repeated in tandem twelve times from the N-terminal to the C-terminal. This dodecapeptide has been shown to contain an immunoreactive region of the protein (Godson, G. N. et al., (1983) Nature 305: 29-33 and Peptide Antigen application). All monoclonal and most of the polyclonal antibodies raised against sporozoites of various species are directed against a domain of the CS molecule. Accordingly, this dodecapeptide is useful in investigation of development of immunity in mammals (including humans) against malaria and in the development of an effective vaccine conferring such immunity, as disclosed in the Peptide Antigen application.

A more precise identification of the immunodominant region in fact of the immunodominant epitope itself, is desirable for several reasons: one is that such identification would be useful in providing a further understanding of the immunogenicity of the CS protein; another is that a peptide with a shorter amino acid sequence identical or related to that of the epitope is easier to prepare and/or purify, using either conventional peptide synthesis or recombinant DNA techniques. Such a peptide would be useful if it displayed anti-CS binding activity similar to that of the dodecapeptide. Of even greater interest was the verification of whether the epitope was represented within an uninterrupted sequence of amino acids in the dodecapeptide or whether it was configurational, i.e., formed by residues juxtaposed by virtue of the higher order structure of the dodecapeptide (12-peptide). Since several monoclonal (and polyclonal) antibodies to the CS protein neutralize the infectivity of sporozoites, if the epitope was represented in an uninterrupted sequence formed of a relatively short sequence, this peptide would provide the basis for the development of a synthetic vaccine.

The size and shape of epitopes found in carbohydrate antigens have been extensively studied in the past, but less is known about the structure of epitopes from protein molecules. Some epitopes of protein antigens have been defined at the level of their 3D structure. In every instance, the epitopes were formed not by the primary sequences alone, but by the juxtaposition of residues brought together by the folding of the polypeptide chain(s) of the native molecule. For example, monoclonal antibodies to sperm whale myoglobin did not react with any of the three CNBr cleavage fragments which collectively encompass the whole sequence of hemoglobin (Berzofsky, J. A. et al., "Topographic Antigenic Determinants Recognized by Monoclonal Antibodies to Sperm Whale Myoglobin" (1982) J. Biol. Chem. 257: 3189-3198; East, I. J. et al, "Antigenic Specificity of Monoclonal Antibodies to Human Myoglobin" (1982) J. Biol. Chem. 257: 3199). A monoclonal antibody bound to the epitope in the lysozyme which was found to include a region containing the Arg 68-Arg 45 complex which borders the catalytic site (Smith-Gill, S. J. et al., "Mapping the Antigenic Epitope for a Monoclonal Antibody Against Lysozyme", (1982) J. Immunol. 128: 314). Monoclonal antibodies which recognize the A-chain loop (A 8-10) of insulin failed to bind to isolated A chains, or to synthetic peptides (Shroer J. A. et al., (1983) Eur. J. Immunol. 13: 693).

OBJECTS OF THE INVENTION

Accordingly, it is an object of this invention to localize and identify the immunodominant epitope(s) of the circumsporozoite (CS) protein. It is a more particular object of this invention to identify the immunodominant epitope(s) of each repeating unit of the tandem repeating peptide of the CS protein, and to determine whether it is represented by a sequence of amino acids.

It is another object of this invention to provide a peptide exhibiting immunochemical reactivity vis a vis monoclonal antibodies to CS protein substantially equivalent to that of the CS protein and peptides or epitopes contained in said protein.

It is also an object of this invention to provide a peptide having the above properties that would be convenient to prepare and/or purify using existing techniques.

It is a further object of this invention to provide a peptide that would be useful in the development of a vaccine against malaria.

It is still a further object of this invention to provide a method for identifying said epitope or analogs thereof.

SUMMARY OF THE INVENTION

According to the present invention, an immunodominant epitope has been identified within the repeating unit of the tandem repetitive polypeptide of circumsporozoite protein of the genus Plasmodium. A peptide has been prepared that is an analog of the repeating unit of said repetitive polypeptide and has an immunochemical reactivity substantially equivalent to that of the full repeating unit of said polypeptide.

DETAILED DESCRIPTION OF THE INVENTION

The approach used in the present invention involved starting with the amino acid sequence of the repetitive peptide of a sporozoite CS protein such as that of *Plasmodium knowlesi*, synthesizing a tandem repeat peptide thereof (twice the number of aminoacids) and analog peptides thereof having progressively smaller sequences (by progressive omission of terminal amino acids), and determining the reactivity of monoclonal antibodies to the CS protein (monoclonal anti-CS) for such peptides and each of their analogs. The objective was to find the shortest analog with high antibody reactivity, thus simultaneously identifying the location of the epitope within the dodecapeptide (if the locus of such epitope was in the primary amino acid sequence) and identifying a peptide having immunochemical reactivity vis-a-vis monoclonal anti-CS similar to that of the dodecapeptide.

The particular tandem repetitive polypeptide chosen for the experimental work of the present invention was that of *P. knowlesi* CS protein. This repetitive polypeptide is a dodecapeptide having the amino acid sequence (from N to C terminus) ($Gln_1$-$Ala_2$-$Gln_3$-$Gly_4$-$Asp_5$-$Gly_6$-$Ala_7$-$Asn_8$-$Ala_9$-$Gly_{10}$-$Gln_{11}$-$Pro_{12}$).

Several monoclonal anti-CS have been raised against the *P. knowlesi* CS protein (as described in the Malaria Vaccine patent application) and were available for testing the immunoreactivity of peptides synthesized herein. However, the fact that both the peptides synthesized or employed in the present work and the antibodies relate to *P. knowlesi*, does not limit the applicability of the present invention to *P. knowlesi* CS protein. Strong evidence exists that CS-proteins of other Plasmodium species also contain tandem repeating peptides and constitute proteins related to the *P. knowlesi* CS protein (even though their amino acid sequences may not be the same). For example, previously reported results of immunological assays indicated that only one area of the CS molecule of *P. vivax*, *P. falciparum*, *P. knowlesi* and *P. berghei* was recognized by all monoclonal anti-CS (raised from CS protein of the same species). In addition, cross-reactivity has been reported between CS proteins of different Plasmodium species and *P. knowlesi* anti-CS (Cochrane, et al, 1982) Proc. Nat'l Acad. Sci. U.S.A. 79:5651). Moreover, Santoro et al, (1982) J. Biol. Chem. 258:334, have reported evidence that the CS proteins of different malaria species are part of a family of structurally related molecules. Thus, it is anticipated that the present invention will be applicable to several Plasmodium species.

In the work leading to the present invention, a synthetic dodecapeptide (corresponding to the *P. knowlesi* CS protein repeating peptide sequence) and a tetraeicosapeptide consisting of a tandem repeat of said dodecapeptide were prepared and tested for anti-CS binding activity with six anti-CS which had been raised following immunization of mice with intact sporozoites, but which were shown to be reactive with a single molecule, the CS protein: Cochrane, A. H. et al, "Monoclonal Antibodies Identify the Protective Antigens of Sporozoites of *Plasmodium knowlesi*" (1982) Proc. Nat'l. Acad. Sci., U.S.A., 79, 5651. The CS protein is stage-and species-specific (Vanderberg, et al, Military Medicine, 304:1183 (1969); Cochrane, A. H., et al, "Antibody Induced Ultrastructural Changes of Malarial Sporozoites" (1969), J. Immunol. 116, 859) distributed uniformly over the entire sporozoite surface and is shed when cross-linked by antibodies Potocnjak, P.. et al, "Monovalent Fragments (Fab) of Monoclonal Antibodies to a Sporozoite Surface Antigen" (1980) J. Exp. Med., 151, 1505.

Previous work had already shown that only one area of the CS molecule of several species was recognized by all homologous monoclonal anti-CS and that this immunodominant region was multivalent with regard to the expression of a single epitope: Zavala, F., et al., (1983) J. Exp. Med. 157: 1947. DNA analysis has shown that the immunogenic region of *P. knowlesi* CS protein consists of a tandem repeat by 12 units of 12 amino acids each (see Peptide Antigen application). Moreover, the epitope recognized by one monoclonal anti-CS (2G3) was included within a single subunit. The synthetic dodecapeptide very effectively inhibited the anti-CS/CS reaction while the 24/MER interacted simultaneously with two molecules of 2G3.

The present work demonstrated that the epitopes reacting with five other monoclonal anti-CS are also represented within the 24/MER. This was useful in determining whether the epitope lay within a sequence of 24 amino acids, prior to testing whether the epitope was contained within the sequence of the 12 amino acids.

Four monoclonal antibodies (2G3, 5H8, 8B8, and 8E11) were used in immunoactivity testing of synthesized shorter length analogs of the 12-peptide. The purpose was further localization and identification of the epitope contained therein.

An 11-amino acid analog was first synthesized, namely analog (2-12) by omission of the N-end Gln residue. The reactivity of (2-12) was compared with that of the (1-12) and found to be substantially equivalent (see Table 3). Subsequently, the reactivities of 3-12, 4-12 and 5-12 were determined and found substantially identical to that of 1-12. However, omission of the 5th amino acid, residue Asp, resulted in a considerable drop in reactivity. It was tentatively concluded that amino acid residues 1 through 3 and possibly 4 did not contribute to the immunoreactivity of the 12-peptide.

Starting from the C-end, the analogs (1-11), (2-11) and (3-11) were not synthesized based on the hypothesis that amino acids 1, 2 and 3 did not contribute to immunoreactivity. (4-11) had immunoreactivity substantially equivalent to (actually, slightly higher than) that of (5-12). However, (5-11) showed a drop in reactivity commensurate with that observed by going from (5-12) to (6-12).

Shorter length peptides showed no reactivity, thus confirming that the (4-11) and (5-12) peptides were those having high reactivity and minimum length.

The above method of omitting one end amino acid at a time and testing the reactivity of the resulting peptide leads to the isolation of the epitope in the minimum number of steps. Once an amino acid residue is shown not to participate in the epitope, it can be eliminated from further testing.

As summarized in Table 3, the dodecapeptide $NH_2$Gln-Ala-Gln-Gly-Asp-Gly-Ala-Asn-Ala-Gly-Gln-ProCONH$_2$ (1-12), as well as the peptides (2-12), (3-12), (4-12) and (5-12) were very efficient inhibitors. However, following removal of Asp or Asp and Gly (positions 5 and 6), the degree of reactivity was considerably lower. This is consistent with the hypothesis that peptides shorter than 5-12 are not active. The role of amino acids from the C-terminal end of (1-12) was also examined. As shown in panel B of FIG. 3, removal of Pro (position 12) or Gln (position 11) from the dodecapeptide had a considerable effect in its reactivity with the monoclonal 5H8. However, for monoclonals 2G3 and 8B8, the reactivity with 4-12 or 4-11 was almost identical, while 4-10 was much less reactive (panel B, FIGS. 4 and 5). The dodecapeptide contains only one proline (at the C-terminus) and this residue is not essential for reactivity with two monoclonal antibodies.

The above results led to the conclusion that (a) contrary to the results of investigation on many other antigens, there is a single immunodominant region in the CS protein of *P. knowlesi* and the epitope is located within a primary sequence (rather than a conformation) of 12 amino acids around residues 4-11; and (b) it is possible to obtain substantially equivalent immunoreactivity from a peptide having only an 8-residue rather than a 12-residue sequence; i.e. it is possible to obtain an immunoreactive peptide of minimum amino acid length, shorter than that of the repeating unit (dodecapeptide) itself.

Figure 1:
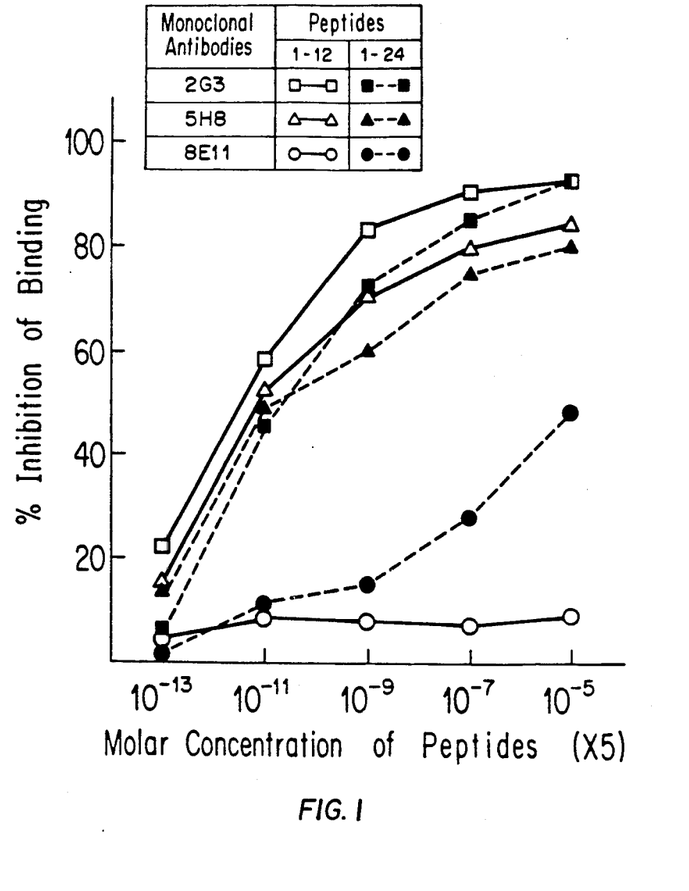
FIG. 1 is a graph depicting the relation between the activity of the dodecapeptide (constituting the repeating unit of the repetitive peptide of the *P. knowlesi* CS protein) and a 24-peptide (consisting of a tandem repeat of said dodecapeptide) inhibiting the binding of different monoclonal antibodies to the *P. knowlesi* C protein.

From the above, it is clear that the monoclonals react with a sequence of amino acids around residues (4-11). FIG. 1 shows that the specificity of 8E11 differs markedly from that of the other monoclonal antibodies in that the interaction of 8E11 with the CS protein is only inhibited by (1-24), and not by (1-12). To examine the possibility that 8E11 recognizes a sequence overlapping between two tandem dodecapeptides of 1-12, several other peptides were synthesized and assayed for inhibitory activity, with negative results. This indicates that 8E11 reacts with a configurational or topographic epitope formed by joining two dodecamers.

Three of the four monoclonal antibodies used in the immunoreactivity tests of the 12-peptide, the 24-peptide and the synthetic analogs (2G3, 5H8 and 8E8) were recognized by the reactive shorter analogs of minimum length. Because the epitope is repeated twice within a sequence of 24 consecutive amino acids, it is not likely that the binding sites recognize secondary or tertiary structures of the polypeptide chain. The striking immunogenicity of this epitope is most likely a reflection of the unusual structure of the CS protein, half of which consists of tandem repeats of 12 amino acids, each repeat containing a potential epitope. It is noteworthy that the streptococcal M protein type 24 also contains a repeated peptide subunit, which contains the immunodominant epitope (Beachey, E. H., et al., "Primary Structure of Protective Antigens of Type 24 Streptococcal M Protein", (1980) J. Biol. Chem. 255: 6284-6289. However, the CS-protein is not known to bear any structural or other similarity to the M-protein.

In other studies, monoclonal antibodies 2G3 and 8E11 (or the corresponding Fab fragments) not only bound to the *P. knowlesi* CS protein, but also neutralized the infectivity of the sporozoites (Cochrane, A. H., et al., supra). In light of the present results, it seemed possible that polyclonal antibodies to synthetic peptides representing the repetitive epitope of the CS protein of *P. knowlesi* could have similar biological activities. Indeed, rabbits and mice have been successfully immunized against *P. knowlesi* with the tetraeicosapeptide (1-24) conjugated to a carrier protein. Several animals made antibodies that reacted with the membrane of sporozoites, and immunoprecipitated the CS protein. In addition, sporozoites lost their infectivity when incubated in the serum from one of the immunized rabbits. These observations raised hopes that if equivalent peptides from the CS proteins of human malaria parasites are found to be immunogenic in vivo, they may be used in the formulation of vaccines for humans.

The general steps of the peptide synthesis techniques used herein are well known. Specific modifications made by the present inventors, to adapt such techniques to the synthesis of the present peptides, are described in the Examples.

After synthesis, cleavage and purification, the peptides were tested for reactivity with monoclonal anti-CS, preferably partially purified. The anti-CS used in these tests were produced by ascites tumor induction using hybridoma cells resulting from the fusion of plasmacytoma cells with spleen cells of a mouse immunized with the parasite, as described by Cochrane, A. H. et al, supra, and as disclosed in the Malaria Vaccine patent application.

The immunoactivity of the synthetic peptides was evaluated by measuring their ability to inhibit the reaction between the monoclonal anti-CS and the antigen (CS protein). Antigen was purified from sporozoites, as disclosed in the Malaria Vaccine patent application and as also described by Vanderberg, supra, and Zavala, F., et al, supra, 1982, is preferably employed using $^{125}$I-labeled antibody.

The present invention is further described below in the following Examples, which are intended to illustrate it but not to limit its scope.

MATERIALS AND SOURCES

Derivatized amino acids (and protective groups) and benzhydrylamine resin: Beckman Instruments, Palo Alto, Calif. hydroxybenzotriazole: Sigma Chemical Co., Inc. St. Louis, Mo. Sephadex G-25 and G-200: Pharmacia Fine Chemicals Co. Piscataway, N.J. bovine serum albumin: Sigma Chemical Co., St. Louis, Mo. Iodogen: Pierce Chemical Co., Rockford, Ill. Boulton-Hunter Reagent: Amersham Corp., Arlington Hgts, Ill.

EXAMPLE 1

Peptide Syntheses

Syntheses were carried out using a benzhydrylamine BHA) resin (0.654 meg/gm) on a Vega model 250C (Vega Biochemicals, Inc., Tuscon, Ariz.) automated synthesizer controlled by a Motorola computer with a program based on that of Merrifield, R. B., Fed. Proc. 21:412 (1962); J. Chem. Soc. 85:2149, (1963). First, the dodecapeptide Gln-Ala-Gln-Gly-Asp-Gly-Ala-Asn-Ala-Gly-Gln-Pro was assembled on 3.0 gms of the benzhydrylamine resin which were suspended in $CH_2Cl_2$ and washed 3 times with $CH_2Cl_2$, 3 times with ethanol, and 3 times with $CH_2Cl_2$ in the synthesizer. The resin was washed for a total of 2 minutes and then treated with 50% trifluoroacetic acid containing 10% anisole in $CH_2Cl_2$ for 30 min, washed ten times with $CH_2Cl_2$, neutralized by washing twice with 10% diisopropylethylamine in $CH_2Cl_2$. The first BOC-amino[1] acid was coupled for one to the benzhydrylamine resin using three-fold molar excess of BOC amino acid dicyclohexyl carbodiimide in the presence of 3 molar excess of $CH_2Cl_2$ and hydroxybenzotriazole. Additional aliquots, one of hydroxybenzotriazole and one of diisopropylethylamine, were added at a three-fold molar excess of BOC amino acid for an additional hour. The resin was then washed with $CH_2Cl_2$ (3 washes), absolute ethanol (3 washes) and $CH_2Cl_2$ (3 washes) and an aliquot of the mixture was tested using the Kaiser ninhydrin procedure (Kaiser, E. et al., (1970), Analyt. Biochem. 34: 595. The resulting peptide was Boc-Gln(NPE)-Ala-Gln(NPE)-Gly-Asp(OBZ)-Gly-Ala-Asn(NPE)-Ala-Gly-Gln(NPE)-Pro-Co-BHA[2].

BOC stands for tertiary butyloxycarbonyl
NPE stands for nitrophenylester
OBZ stands for o-benzyl At this point in the synthesis, 50% of the protected peptide resin was removed and saved for HF cleavage and purification.

The tandem repeat; i.e., the tetraeicosapeptide (1-24) was assembled by the sequential addition of protected amino acids in the same order as for the dodecapeptide, using the above-described method.

Following synthesis, 2.0 gms each of the (1-12) and (1-24) protected peptide resins were subjected to treatment with HF as described below and the deprotected cleaved peptides were washed separately with anhydrous ether and extracted with alternate washes of glacial acetic acid and water.

Cleavage of the peptide-resins (2gms each) was performed in a Penninsula HF apparatus (Penninsula, Laboratory, San Carlos, Calif.) in the presence of anisole (1.2 ml/mg resin) and methyl ethyl sulfide (1 ml/mg) at 0° C. for one hour after which the mixture was thoroughly dried under high vacuum. The mixture was then washed with cold anhydrous ether, extracted with alternate washes of water and glacial acetic acid and lyophilized.

The crude peptides were then desalted by gel filtration on Sephadex G-25 (120 ×2.0 cm) in 200 mg aliquots. The column was equilibrated with 0.1 $NH_4HCO_3$ pH 8.0, also used as the sample buffer. Column effluent was monitored by UV absorbance at 254 and 206 nm with an LKB UV-Cord III monitor.

The peptides thus synthesized, were analyzed and characterized as follows:

Samples were hydrolyzed in 5.7 N HCl for 22 hours at 110° C., dried, reconstituted in 0.2 N sodium citrate, pH 2.2 and applied to the amino acid analyzer (Liquimat III) according to the method of Spackman, D. H. et al, Anal. Chem., 30:1190, 1958.

At selected steps during synthesis, aliquots of the peptide resin were removed from the reaction vessel of the synthesizer mixed with glass beads, subjected to automated solid phase Edman degradation (Laursen, R., Eur. J. Biochem 20:29 1971) on a Sequemat Mini 15 peptide sequencer (Sequemat, Inc. Waltham, Mass.). Following cleavage of the peptide from the resin, crude and purified synthetic peptides were subjected to automated liquid phase sequence analysis (Edman P. and Begg G., Eur. J. Biochem. 1:80–90 (1967)) on a Beckman (Model 890) sequencer using a "DMAA" (dimethylallylamine) peptide program to detect the presence of failure sequence and of side chain protecting groups on the peptide that had not been removed by HF cleavage. Quantification of the amount of error peptides and side chain protecting groups was assessed by sequence analysis, followed by identification and quantification of the PTH amino acids by high performance liquid chromatography, a well accepted method of "preview" analysis as disclosed by Niall, H. D., et al., "Chemistry & Biology of Peptides: Proceedings of the Third American Peptide Symposium (1972) (J. Meienhofer, ed.) Ann Arbor Science Pub., 695 1972; modified by Tregear, G. W., "Peptides: Proceedings of the Third European Peptide Symposium" (Y. Wolman, ed.,) (1974; and Tregear, G. W., et al., Jr. Biochem. (1977) 16: 2817; as further modified by (Simmons, J. and Schlesinger, D. H., "High-Performance Liquid Chromatography of Side-ChainProtected Amino Acid Phenylthiohydantoins", (1980) Anal. Biochem., 104, 254; and Schlesinger, D. H., (1983), Meth. Enzymol. 91, 494.

In addition to the dodecapeptide and 24-peptide, four groups of peptide analogs of the dodecapeptide were synthesized, each possessing as the C-terminal amino acid either Pro, Gln, Gly or Ala, which correspond to positions 12, 11, 10 and 9 respectively, of the dodecamer (Table 1). The peptide analogs possessing Pro at their C-terminus were synthesized by removing dried protected peptide resin (approximately 10% at each step) at positions 10, 8, 7, 6, 5, 4, 3 and 2 during the synthesis of the dodecapeptide, as described above. This procedure yielded 9 protected peptide resins.

Similarly, two peptides were synthesized containing the C-terminal amino acid Gln; i.e., peptides comprising residues in positions 5-11 and 4-11 of the dodecamer. Only one peptide containing Gly at its C-terminus was synthesized, and it corresponded to positions 4-10 of the dodecamer. Finally, four peptides possessing Ala at their C-terminus (positions 7-9, 6-9, 5-9 and 4-9 of the dodecapeptide) were synthesized in analogous fashion. One peptide which bridges parts of two epitopes was synthesized, i.e., $Ala_7$-$Asn_8$-$Ala_9$-$Gly_{10}$-$Gln_{11}$-$Pro_{12}$-$Gln_1$-$Ala_2$-$Gln_3$-$Gly_4$-$Asp_5$-$Gly_6$ to determine if monoclonal antibody which might not recognize the dodecapeptide or any of the above analogs might be directed against a sequence containing parts of two tandem repeats.

These protected peptide-resins were then cleaved and deprotected with HF, desalted on Sephadex G-25 and characterized by amino acid composition and sequencing preview analysis (see Table I, below). The peptides were used in immunological studies without further purification.

EXAMPLE 2

Reaction of Monoclonal Antibodies with the Tetraeicosapeptide

Monoclonal antibodies against surface antigens of sporozoites of the simian malaria parasite *Plasmodium knowlesi* were produced by fusion of plasmacytoma cells with spleen cells of a mouse immunized witn the parasite as previously described by Cochrane et al., supra., (1982) and described in detail in the Malaria Vaccine patent application. The monoclonal antibodies (four idiotypes: 2G3, 8B8, 5H8 and 8E11 were partially purified from ascites of mice bearing hybridomas by 50% ammonium sulphate precipitation followed by molecular sieve chromatography on Sephadex G-200.

All types of monoclonal antibodies which were raised against *P. knowlesi*, and selected for reactivity with the surface membrane of the parasite (Cochrane et al., 1982) reacted with the tetraeicosapeptide.

Competitive inhibition of the antigen-antibody reaction by the thus synthesized peptides was measured by the following radioimmunoassay. *P. knowlesi* sporozoite CS protein was used as the antigen.

(a) Preparation of antigen: 3,000 purified *P. knowlesi* sporozoites (Vanderberg et al., Military Medicine 134:1183, 1969) in 50 $\mu$l of phosphate buffered saline (PBS) containing protease inhibitors, were delivered to the bottom of polystyrene (Falcon 3911 plate, B-D and Co., Oxnard, Calif.) microtiter plates, which were sealed with parafilm and frozen at $-70°$ C. for at least ten minutes. The plates were then allowed to defrost slowly at room temperature. This procedure was repeated six times. Then the plates were incubated at 4° C. overnight, and at 56° C. for five minutes. The *P. knowlesi* extract was then removed from the wells and these were washed three times with PBS containing 1% bovine serum albumin (BSA) and 0.1% $NaN_3$. The wells were then filled with PBS-BSA-$NaN_3$ for a few hours at room temperature.

(b) Preparation of peptides and two-site radioimmunoassay to determine the inhibitory activity of the analogs.

All synthetic peptides were dissolved in PBS at a concentration of 10 mM and subsequently diluted serially in PBS-1% BSA/0.1% $NaN_3$. Twenty-five $\mu$l of serial dilutions of each peptide were added to the wells coated with antigen. Control wells received only the diluent. Then, 25 $\mu$l of the $^{125}$I-labelled monoclonal antibody (about 5-10ng, 10 $^5$cpm) were added to the wells. The microtiter plates were incubated at 4° C. for 18 hours, washed 5 times with PBS-BSA-$NaN_3$ and then the wells were counted for well-bound antibody. (LKB 1260 Muilti-gamma $\gamma$-counter LKB Instruments, Inc., Gaithersburg, Md.).

The antibodies (above) and peptides (below) were labeled with $^{25}$I using Iodogen (Pierce Chemical Co., Rockford, Ill.) or Boulton-Hunter reagent (Amerisham Corp., Arlington, Hts., Ill.), according to the instructions of the manufacturers.

To determine whether the 24-peptide is recognized by all monoclonal antibodies, 5 mg of purified monoclonal antibodies were bound to 1 ml of CNBr activated Sepharose 4B (Pharmacia Fine Chemicals, Piscataway, N.J., U.S.A.) according to instructions of the manufacturer. The 24 amino acid peptide was radiolabelled with $^{125}$I with the Boulton-Hunter reagent, to a specific activity of approximately $10^4$ cpm/$\mu$g. Twenty $\mu$l of beads bearing the different antibodies were incubated for 60 minutes at room temperature in the presence of 100 $\mu$l of PBS-BSA containing either 1 $\mu$g of the radiolabelled peptide alone or radiolabelled peptide in the presence of 200 g of cold tetraeicosapeptide. The beads were then washed by centrifugation with PBS-BSA and counted in a gamma-counter.

Table 2 shows that the radiolabelled (1-24) bound specifically to monoclonal antibodies 2G3, 5H8, 8B8 and 8A8 coupled to Sepharose beads. The binding was totally inhibited by adding an excess of cold (1-24) to the incubation mixture. Analogous results were obtained in other experiments using monoclonal antibodies 8E11 and 6B8 (not shown).

EXAMPLE 3

Localization of the Epitope within the Tetraeicosapeptide

The inhibiting activity of (1-12) and (1-24) on the binding of the radiolabelled antibodies to the *P. knowlesi* sporozoite CS protein extracted as described in Example 2 was investigated. The antigen was immobilized on the microtiter wells. FIG. 1 demonstrates that for two out of three monoclonal antibodies tested (2G3, 5H8) the epitope must be contained within (1-12), since the inhibitory activities of (1-12)—designated by the white symbols—and (1-24) were almost identical. Similar results were obtained with 8B8 but are not shown in this Figure. By contrast, the binding of antibody 8E11 was inhibited only by (1-24).

EXAMPLE 4

Epitope Recognition by Monoclonal Antibodies 2G3, 5H8 and 8B8

Figure 2:
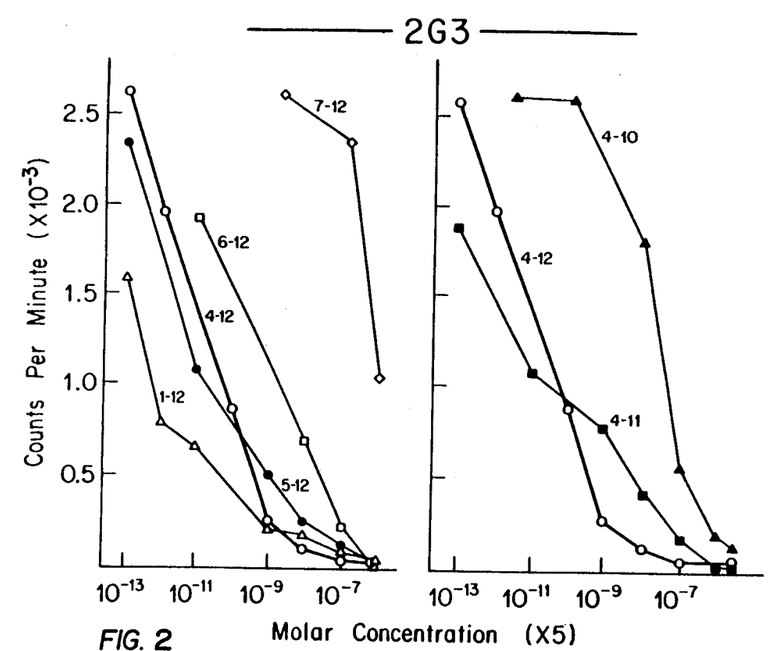
FIG. 2 is a graph depicting the inhibition of the binding of monoclonal antibody 2G3 to *P. knowlesi* CS protein by peptides which are analogs of the repetitive peptide of the CS proteins, said peptides being designated by the position of their terminal amino acids within the sequence of the dodecapeptide.
Figure 3:
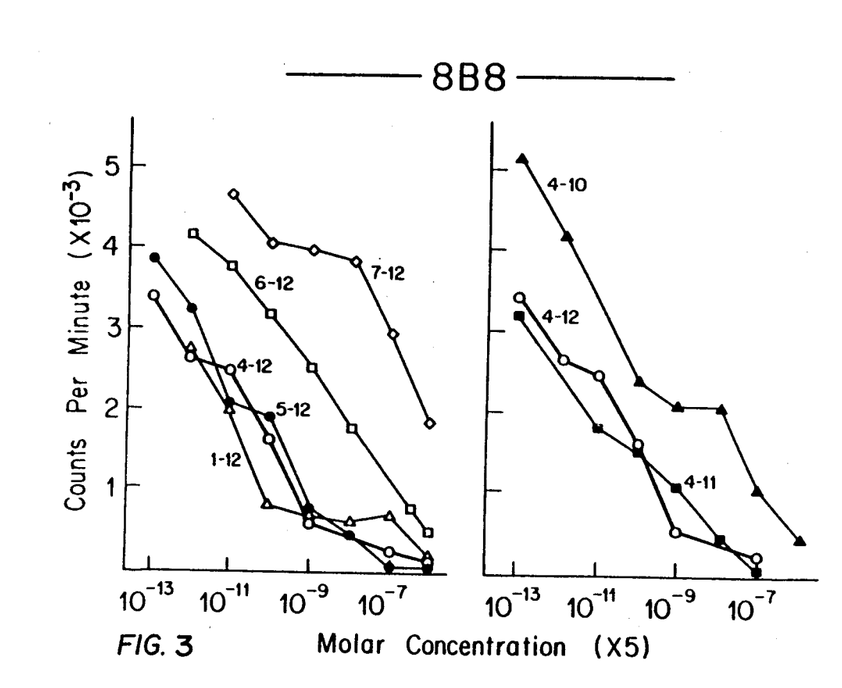
FIG. 3 is a graph depicting the inhibition of binding of radiolabelled monoclonal antibody 5H8 to *P. knowlesi* CS protein in the presence of increasing concentrations of various peptides, said peptides being designated as in FIG. 2.
Figure 4:
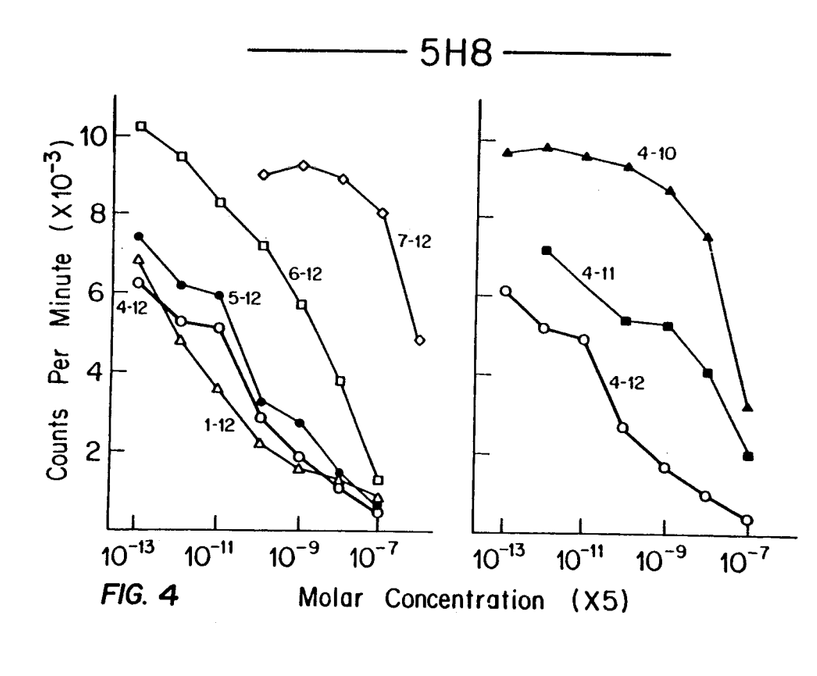
FIG. 4 depicts inhibition of binding of radiolabelled monoclonal antibody 8B8 to *P. knowlesi* CS protein in the presence of increasing concentrations of various peptides, designated by their position within the dodecapeptide as in the previous figures.

The series of shorter analogs and one peptide overlapping two epitopes (7-6) shown in Table 1 was used to analyze the specificity of the 2G3, 5H8, and 8B8 antibodies using the inhibition immunoassays described in Examples 2 and 3. As shown in FIGS. 2, 3, and 4, and summarized in Table 3, the patterns of reactivity of these antibodies were strikingly similar. The peptides (1-12), (2-12), (3-12), (4-12), (5-12) were strongly inhibitory and as effective as (1-24). On a molar basis, their activities were similar, although in some instances the larger peptides appeared to be slightly better inhibitors. However, a considerable drop in activity was observed in (6-12) and (7-12) as compared to (5-12). These results indicate the presence of an immunodominant epitope around the segment $Asp_5$-Gly-Ala-Asn-Ala-Gly-Gln-$Pro_{12}$. determine the participation of the C-terminal amino acids, the activity of (4-10) and (4-11) was compared to that of (4-12). As also shown in FIGS. 2, 3, and 4, the removal of proline (peptide 4-11) had little effect on the reactivity with monoclonal antibodies 2G3 and 8B8, while removal of both glutamine and proline (4-10) diminished markedly the capacity to inhibit the reaction of all three antibodies with the antigen. The shorter peptides (4-9), (5-9), (6-9), (7-9), (8-12), (9-12), and (10-12) were virtually inactive.

EXAMPLE 5

Epitope Recognition by Monoclonal Antibody 8E11

As mentioned above, the reaction of antibody 8E11 with the CS protein of P. knowlesi was inhibited by (1-24). About 50% inhibition of binding of radiolabelled 8E11 to the CS protein was observed with a concentration of (1-24) of $10^{-5}$M. In contrast (1-12) had no appreciable inhibitory effect at a concentration of $10^{-2}$M (See FIG. 1).

EXAMPLE 6

The peptide:

$Ala_7$-$Asn_8$-$Ala_9$-$Gly_{10}$-$Gln_{11}$ -$Pro_{12}$-$Gln_1$-$Ala_2$-$Gln_3Gly_4$-$Asp_5$-$Gly_6$ was synthesized as described above. Assayed as in the foregoing Examples, this peptide was found to be inactive.

TABLE 1

Amino acid composition and preview analysis of synthetic peptide segments of the CS protein P. knowlesi

| Peptide Segment | Asp | Pro | Glu | Gly | Ala | Preview |
|---|---|---|---|---|---|---|
| 1-12 | 1.84(2) | 0.95(1) | 3.00(3) | 3.00(3) | 2.97(3) | 1.4% |
| 2-12 | 2.21(2) | 0.85(1) | 2.15(2) | 3.00(3) | 3.02(3) | N.R. |
| 3-12 | 2.18(2) | 1.07(1) | 2.00(2) | 2.77(3) | 1.88(2) | N.R. |
| 4-12 | 2.00(2) | 1.10(1) | 0.88(1) | 2.84(3) | 1.97(2) | N.R. |
| 5-12 | 2.18(2) | 1.17(1) | 1.00(1) | 2.00(2) | 1.93(2) | N.R. |
| 6-12 | 0.93(1) | 1.00(1) | 0.97(1) | 2.13(2) | 2.16(2) | N.R. |
| 7-12 | 0.90(1) | 1.14(1) | 1.03(1) | 1.00(1) | 2.00(2) | N.R. |
| 8-12 | 0.92(1) | 1.05(1) | 1.01(1) | 1.00(1) | 1.00(1) | N.R. |
| 10-12 | — | 1.10(1) | 1.01(1) | 1.00(1) | — | N.R. |
| 1-24 | 4.15(4) | 1.97(2) | 6.14(6) | 6.05(6) | 5.95(6) | 2.1% |
| 4-11 | 2.16(2) | — | 0.88(1) | 3.40(3) | 2.00(2) | N.R. |
| 5-11 | 2.06(2) | — | 0.95(1) | 2.21(2) | 2.01(2) | N.R. |
| 4-10 | 1.88(2) | — | — | 3.00(3) | 1.75(2) | N.R. |
| 4-9 | 2.00(2) | — | — | 2.18(2) | 1.97(2) | N.R. |
| 5-9 | 2.00(2) | — | — | 0.81(1) | 2.14(2) | N.R. |
| 6-9 | 1.00(1) | — | — | 0.75(1) | 2.15(2) | N.R. |
| 7-9 | 1.00(1) | — | — | — | 2.21(2) | N.R. |
| 7-6* | 1.94(2) | 0.89(1) | 3.06(3) | 2.95(3) | 2.91(3) | N.R. |

*peptide bridging two epitopes, i.e.
$Ala_7Asn_8Ala_9Gly_{10}Gln_{11}Pro_{12}Gln_1Ala_2Gln_3Gly_4Asp_5Gly_6$

TABLE 2

Binding of $^{125}$I-labelled tetraeicosa-peptide (24 amino acids) to different monoclonal antibodies raised against the sporozoite surface protein of P. knowlesi

| Beads bearing the following monoclonal antibodies against the surface protein of P. knowlesi | cpm (% of input) of radiolabelled tetraeicosa peptide that bound to the beads suspended in: | |
|---|---|---|
| | PBS-BSA | PBS-BSA + excess of cold tetraeicosapeptide |
| 2G3 | 2922 (25.8) | 25 (0.2) |
| 5H8 | 2332 (19.7) | 20 (0.2) |
| 8B8 | 3155 (27.8) | 20 (0.2) |
| 8A8 | 1092 (10.3) | 25 (0.2) |
| Control: beads | 25 (0.2) | 0 |
| bearing a monoclonal antibody (3D11) against the surface protein of P. berghei | | |

TABLE 3

Inhibitory effect of synthetic peptides on the binding of radiolabeled monoclonal antibodies to the CS protein P. knowlesi

| Peptide | Molar concentration of peptide (×5) necessary for 50% inhibition of binding of monoclonal antibody | | |
|---|---|---|---|
| | 8B8 | 2G3 | 5H8 |
| 1-12 | $10^{-12}$ | $10^{-13}$ | $10^{-12}$ |
| 2-12 | $10^{-12}$ | $10^{-12}$ | $10^{-11}$ |
| 3-12 | $10^{-12}$ | $10^{-12}$ | $10^{-11}$ |
| 4-12 | $10^{-12}$ | $10^{-11}$ | $10^{-12}$ |
| 5-12 | $10^{-12}$ | $10^{-11}$ | $10^{-11}$ |
| 6-12 | $10^{-10}$ | $10^{-10}$ | $10^{-9}$ |
| 7-12 | $10^{-7}$ | $10^{-6}$ | $10^{-6}$ |
| 4-10 | $10^{-10}$ | $10^{-5}$ | $10^{-7}$ |
| 4-11 | $10^{-12}$ | $10^{-12}$ | $10^{-10}$ |

What is claimed is:

1. A peptide consisting essentially of an amino acid sequence, said sequence defining an immunodominant epitope of a repeating unit of a tandem repetitive polypeptide circumsporozoite protein of a member of the genus Plasmodium, said peptide being shorter in length than said repeating unit.

2. The peptide of claim 1, wherein said circumsporozoite protein is of *Plasmodium knowlesi*.

3. The peptide of claim 2 wherein said polypeptide has the amino acid sequence ($Gln_1$-$Ala_2$-$Gln_3$-$Gly_4$-$Asp_5$-$Gly_6$-$Ala_7$-$Asn_8$-$Ala_9$-$Gly_{10}$-$Gln_{11}$-$Pro_{12}$) from the N to the C terminus of said polypeptide.

4. The peptide of claim 3 amino acid sequence consisting of Asp-Gly-Ala-Asn-Ala-Gly-Gln and at least one of (a) Gly adjacent to and preceding said Asp and (b) Pro adjacent to and following said Gln.

5. A peptide having the amino acid sequence Asp-Gly-Ala-Asn-Ala-Gly-Gln-Pro.

6. A peptide having the amino acid sequence Gly-Asp-Gly-Ala-Asn-Ala-Gly-Gln.

7. The peptide of claim 1, said peptide being immunochemically reactive with at least two monoclonal antibodies to said circumsporozoite protein.

8. A peptide according to claim 1, wherein the member of the genus Plasmodium is selected from the group consisting of *P. falciparum, P. vivax, P. knowlesi, P. malariae, P. cynomolgi, P. berghei,* and *P. yoeli nigeriensis*.

9. A vaccine for immunizing a mammal against malaria comprising as an active ingredient the peptide of claim 1 and a suitable carrier.

10. A vaccine according to claim 9 wherein said peptide is adsorbed or covalently attached to a carrier protein.

* * * * *